United States Patent [19]

Witkowski et al.

[11] Patent Number: 4,528,291
[45] Date of Patent: Jul. 9, 1985

[54] 2-(4'-PYRIDINYL)-THIAZOLE COMPOUNDS AND THEIR USE IN INCREASING CARDIAC CONTRACTILITY

[75] Inventors: Joseph T. Witkowski, Morris Township, Morris County; Brooks R. Sunday, Oakland, both of N.J.

[73] Assignee: Schering Corporation, Kenilworth, N.J.

[21] Appl. No.: 391,061

[22] Filed: Jun. 22, 1982

[51] Int. Cl.$^3$ .................. C07D 417/04; A61K 31/425
[52] U.S. Cl. .................................. 514/301; 546/276; 546/280
[58] Field of Search ............... 424/263; 546/280, 276; 514/301

[56] References Cited

U.S. PATENT DOCUMENTS 3,980,659  9/1976  Fleckenstein et al. .............. 424/263
4,260,609  4/1981  Baldwin et al. ..................... 546/280

OTHER PUBLICATIONS

Chemical Abstracts, vol. 49, 6952, 1954, Jan Bartz et al.

*Primary Examiner*—Henry R. Jiles
*Assistant Examiner*—J. G. Mullins
*Attorney, Agent, or Firm*—Anita W. Magatti; Stephen I. Miller

[57] ABSTRACT

The pyridinyl-thiazole derivatives of the present invention exhibit good cardiotonic activity.

19 Claims, No Drawings

2-(4'-PYRIDINYL)-THIAZOLE COMPOUNDS AND THEIR USE IN INCREASING CARDIAC CONTRACTILITY

BACKGROUND

This invention relates to certain 2-(4'-pyridinyl)-thiazole compounds which are useful in increasing cardiac contractility, to pharmaceutical compositions containing such compounds, and to a method of treating a patient by administering an effective amount of such compounds to increase cardiac contractility in said patient.

Various pyridinyl-thiazoles are known in the art. For example, U.S. Pat. Nos. 3,821,384 and 3,842,172 describe various 2-(3'-pyridinyl)-thiazoles useful as antiaggression agents. U.S. Pat. No. 3,852,293 describes certain 2-(3'-pyridinyl)-thiazoles as anti-inflammatory agents. Liebigs Ann. Chem. 717, 148–153 (1968) and Chem. Abstract 70:37693Z teaches various 2(4'-pyridinyl)-thiazoles none of which are claimed herein as potential tuberculostatic agents.

United Kingdom Pat. No. 1,382,854 describes various 2-(3'-pyridinyl)thiazole derivatives as possessing insecticidal activity.

Journal of Organic Chemistry, 22, 984–986 (1957) describes the 4-methyl-2(4'-pyridinyl)-thiazole and 4-hydroxy-5-methyl-2-(4'-pyridinyl)-thiazole.

Journal of Medicinal Chemistry, 23, 65–70 (1980) also describes the 4-hydroxy-5-methyl-2-(4'-pyridinyl)-thiazole.

SUMMARY OF THE INVENTION

The invention relates to certain 2-(4'-pyridinyl)-thiazole compounds which are useful in increasing cardiac contractility, to compositions containing these compounds and to the method of using these compounds.

The compounds of the present invention are substituted or unsubstituted 2-(4'-pyridinyl)-thiazoles or the N-oxides thereof which are represented by the formula:

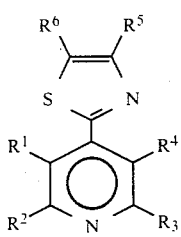

wherein
A. $R^1$, $R^2$, $R^3$ and $R^4$ are independently selected from
 (i) hydrogen,
 (ii) halogen,
 (iii) lower alkyl,
 (iv) lower alkoxy,
 (v) hydroxy, and
 (vi) amino;
B. $R^5$ and $R^6$ are independently selected from
 (i) hydrogen with the proviso that $R^5$ and $R^6$ are not both hydrogen,
 (ii) lower alkyl with the proviso that when $R^1$, $R^2$, $R^3$, $R^4$ and $R^6$ are hydrogen $R^5$ is not lower alkyl,
 (iii) lower alkoxy,
 (iv) hydroxy with the proviso that when $R^1$, $R^2$, $R^3$ and $R^4$ are hydrogen and $R^5$ is hydroxy, $R^6$ is not lower alkyl,
 (v) $-NR^7R^8$ wherein $R^7$ and $R^8$ are the same or different and are independently selected from lower alkyl or hydrogen,
 (vi) trifluoromethyl,
 (vii) hydroxy lower alkyl,
 (viii) cyano,
 (ix)

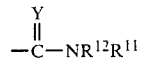

wherein $R^{11}$ and $R^{12}$ are the same or different and are independently selected from hydrogen, lower alkyl and hydroxyloweralkyl, and Y is oxygen or sulfur;
 (x)

C. the pyridinyl-N-oxides thereof; and
D. pharmaceutically acceptable salts thereof.

Preferred $R^1$, $R^2$, $R^3$ and $R^4$ substituents are hydrogen and lower alkyl.

Most preferably, the $R^1$, $R^2$, $R^3$ and $R^4$ lower alkyl substituent is methyl.

Preferred $R^5$ and $R^6$ substituents include, amino, hydrogen, hydroxy, cyano and

wherein $R^{11}$ and $R^{12}$ are independently hydrogen or lower alkyl.

Most preferably $R^5$ is

Preferably Y is oxygen.

Representative compounds of this invention include for instance:
4-methyl-2-(4'-pyridinyl)-thiazole-5-carboxamide;
N-methyl-2-(4'-pyridinyl)-thiazole-4-carboxamide;
2-(4'-pyridinyl)-thiazole-4-carboxamide;
4-cyano-2-(4'-pyridinyl)-thiazole;
4-methyl-5-cyano-2-(4'-pyridinyl)-thiazole;
4-amino-2-(4'-pyridinyl)-thiazole;
N-methyl-4-amino-2-(4'-pyridinyl)-thiazole;
2-(4'-pyridinyl)-thiazole-4-carboxamidine hydrochloride;
4-ethoxy-2-(4'-pyridinyl)-thiazole;
2-(3'-amino-4'-pyridinyl)-thiazole-5-carboxamide;
4-methyl-2-(4'-pyridinyl)-thiazole-5-carboxamide;
4-ethyl-2-(4'-pyridinyl)-thiazole-5-thio-carboxamide;
N-methyl-2-(2'-methyl-6'-bromo-4'-pyridinyl)-thiazole-5-carboxamide;
5-methyl-4-trifluoromethyl-2-(2'-n-propyl-4'-pyridinyl)-thiazole;
5-ethyl-4-trifluoromethyl-2-(2'-methyl-3'-chloro-4'-pyridinyl)-thiazole;
4-hydroxy-2-(2'-methoxy-4'-pyridinyl)-thiazole;
4-hydroxy-2-(2'-n-propoxy-4'-pyridinyl)-thiazole;

4-hydroxy-2-(2'-hydroxy-3'-bromo-4'-pyridinyl)-thiazole;
5-hydroxy-2-(3'-hydroxy-4'-pyridinyl)-thiazole and
N-ethyl 2-(4'-pyridinyl)thiazole-5-carboxamide;
N-ethyl 4-ethyl-2-(4'-pyridinyl)thiazole-5-carboxamide;
N-ethyl 4-n-propyl-2-(4'-pyridinyl)thiazole-5-carboxamide;
N-methyl 4-methyl-2-(4'-pyridinyl)thiazole-5-carboxamide;
N-n-propyl 5-methyl-2-(4'-pyridinyl)thiazole-4-carboxamide;
N-n-hexyl 5-ethyl-2-(4'-pyridinyl)thiazole-4-carboxamide;
N-methyl 5-n-propyl-2-(4'-pyridinyl)thiazole-4-carboxamide;
N,N-diethyl 5-propoxy-2-(4'-pyridinyl)thiazole-4-carboxamide;
N,N-dimethyl 5-methoxy-2-(4'-pyridinyl)thiazole-4-carboxamide;
N-ethyl N-methyl 5-cyano-2-(2',3'-dimethyl-4'-pyridinyl)-thiazole-4-carboxamide;
N-isopropyl 5-cyano-2-(3'-ethyl-4'-pyridinyl)thiazole-4-carboxamide;
N-Ethyl 5-(2"-hydroxyethyl)-2-(4'-pyridinyl)thiazole-4-carboxamide;
N-Methyl 5-methyl-2-(4'-pyridinyl)thiazole-4-carboxamide;
N,N-dimethyl 5-methyl-2-(3'-methyl-4'-pyridinyl)-thiazole-4-carboxamide;
N,N-diethyl 2-(3'-methyl-4'-pyridinyl)-thiazole-4-carboxamide;
N-n-hexyl-N-ethyl 2-(4'-pyridinyl)-thiazole-5-carboxamide;
N-isopropyl-N-ethyl 4-ethyl-2-(4'-pyridinyl)-thiazole-5-carboxamide;
N-ethyl 4-n-propyl-2-(4'-pyridinyl)-thiazole-5-carboxamide;
N-n-propyl 5-methyl-2-(4'-pyridinyl)-thiazole 4-carboxamide;
N-n-Hexyl 5-ethyl-2-(4'-pyridinyl)-thiazole-4-carboxamide;
N-ethyl 5-cyano-2-(4'-pyridinyl)-thiazole-4-carboxamide;
N-ethyl 4-hydroxy-2-(4'-pyridinyl)-thiazole-5-carboxamide;
5-hydroxy-4-methyl-2-(4'-pyridinyl)-thiazole.
2-(4'-pyridinyl)thiazole-5-carboxamide;
4-methyl-2-(4'-pyridinyl)thiazole-5-carboxamide;
N-ethyl-2-(4'-pyridinyl)thiazole-5-carboxamide;
N-methyl 5-methyl-2-(4'-pyridinyl)thiazole-4-carboxamide;
N,N-dimethyl 5-methyl-2-(4'-pyridinyl)thiazole-4-carboxamide;
N-ethyl 5-cyano-2-(4'-pyridinyl)thiazole-4-carboxamide;
N-(2"-hydroxyethyl) 5-methoxy-2-(4'-pyridinyl)-thiazole-4-carboxamide;
N-n-propyl 5-cyano-2-(3'-ethyl-4'-pyridinyl)-thiazole-4-carboxamide;
N,N-di-n-propyl-5-methyl-2-(4'-pyridinyl)thiazole-4-carboxamide;
5-cyano-2-(4'-pyridinyl)-thiazole;
5-ethyl-4-cyano-2-(4'-pyridinyl)thiazole.
4-hydroxy-2-(2'-methoxy-4'-pyridinyl-N'-oxide)-thiazole;
5-hydroxy-2-(3'-hydroxy-4'-pyridinyl-N'-oxide)-thiazole;
5-hydroxy-4-methyl-2-(4'-pyridinyl-N'-oxide)-thiazole; and
5-ethyl-4-trifluoromethyl-2(2'-methyl-3'-chloro-4'-pyridinyl-N'-oxide)-thiazole.
N,N-diethyl-5-amino-2-(4'-pyridinyl)-thiazole;
N,N-di-n-propyl-5-amino-4-methyl-2-(4'-pyridinyl)-thiazole;
4-amino-2-(3'-chloro-4'-pyridinyl)-thiazole;
5-amino-4-ethoxy-2-(4'-pyridinyl)-thiazole;
4-amino-5-ethoxy-2-(4'-pyridinyl)-thiazole; and
5-amino-4-methyl-2-(4'-pyridinyl)-thiazole.
2-(4'-pyridinyl)-thiazole-5-carboxamidine hydrochloride;
4-methyl-2-(4'-pyridinyl)-thiazole-5-carboxamidine hydrochloride;
4-ethyl-2-(4'-pyridinyl)-thiazole-5-carboxamidine hydrochloride; and
5-ethyl-2-(4'-pyridinyl)-thiazole-4-carboxamidine hydrochloride
5-methyl-2-(4'-pyridinyl)-thiazole-4-thiocarboxamide;
5-methoxy-2-(3'-chloro-4'-pyridinyl)-thiazole-4-thiocarboxamide;
2-(4'-pyridinyl)-thiazole-5-thiocarboxamide; and
2-(4'-pyridinyl-N-oxide)-thiazole-4-carboxamide.

Preferred compounds of this invention are:
2-(4'-pyridinyl)-thiazole-4-carboxamide; and
4-cyano-2-(4'-pyridinyl)-thiazole.

Unless otherwise stated, the term "alkyl" includes both branched- and straight-chain alkyl groups. The term "lower alkyl" includes alkyl groups of from 1 to 6 carbons and includes for instance methyl, ethyl, n-propyl, iso-propyl, t-butyl, n-hexyl and the like.

The term "lower alkoxy" includes both branched- and straight-chain alkoxy of 1 to 6 carbons and includes, for instance, methoxy, ethoxy, isopropoxy, t-butoxy, n-hexoxy and the like.

The term "halogen" refers to the groups fluoro, chloro, bromo and iodo.

The term "hydroxy lower alkyl" refers to those hydroxyalkyl groups wherein the alkyl group is of 1 to 6 carbons and includes for instance 2-hydroxyethyl (i.e. —CH$_2$CH$_2$OH), 2-hydroxy-n-propyl

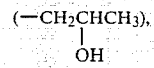

3-hydroxy-n-propyl (—CH$_2$CH$_2$CH$_2$OH) and the like.

The term "pharmaceutically acceptable salts" includes the pharmaceutically acceptable acid addition salts of the compounds of formula I derived from a variety of organic and inorganic acids, such as sulfuric, phosphoric, hydrochloric, hydrobromic, sulfamic, citric, lactic, oleic, succinic, tartaric, cinnamic, acetic, benzoic, gluconic, ascorbic and the like.

The term "thiazole" refers to the group:

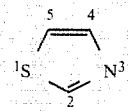

with the conventional numbering shown therewith. Thus the term "4-cyano-2-(4'-pyridinyl)-thiazole" refers to the group:

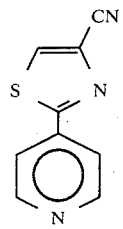

2-(2'-hydroxy-4'-pyridinyl)-thiazoles derivatives are tautomeric with 2-(1H)pyridinones as shown below:

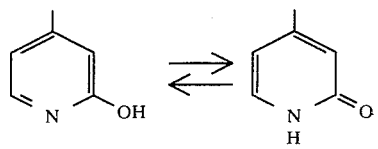

Throughout this disclosure, the term 2-(2'-hydroxy-4'-pyridinyl) shall be taken to mean any of the above tautomers.

DETAILED DESCRIPTION OF THE INVENTION

The compounds of this invention have been found to increase cardiac contractility. As such, the compounds of this invention are useful in the treatment of congestive heart failure.

The compounds of this invention were tested for their ability to increase cardiac contractility both in vitro and in vivo.

In vitro tests were conducted on left atria obtained from guinea pigs employing the method described in Am. J. Physiology 221:1470–1475 (1971). Increases in cardiac contractility were found at concentrations ranging from 1 μgm/ml to 1000 μgm/ml with increases in cardiac contractility found generally from 10 μgm/ml to 100 μgm/ml.

In vivo tests were conducted on open-chest barbituated-anesthetized dogs employing the method described in J. Pharmacology Exp. Ther. 218, 442–452 (1982). Increases in cardiac contractility were generally found at dosage levels of 1 mg/kg to 10 mg/kg.

The present invention contemplates a method for increasing cardiac contractility in a patient requiring such treatment which comprises administering either orally or parenterally an amount effective in increasing cardiac contractility of a compound of Formula I.

Typically, a daily dosage regimen would generally be 0.1 to 1 gm/day oral and 0.05 to 0.5 gm/day parenterally. The actual dose to be administered is determined by the clinician and is dependent upon various factors such as the particular compound employed, age and weight of the subject the severity of the disease and the individual's response.

The compounds are preferably administered either orally or parenterally with the preferred mode of administration dependent on the severity of the individual's condition. For example with an individual suffering an acute case of congestive heart failure the preferred mode of administration would be parenterally while for a chronic case of heart failure, the preferred mode of administration would be orally. The compounds may be combined with any suitable pharmaceutical carrier and administered in a variety of formulations. The compounds may also be administered transdermally.

The methods of this invention are implemented using pharmaceutical compositions comprising a pharmaceutically acceptable carrier and an amount effective in increasing cardiac contractility of a compound of formula I.

In treating certain patients with the compounds of this invention, it is possible to include other pharmaceutically active ingredients in the same dosage unit.

The compounds of this invention were also found in vivo to modestly reduce blood pressure while increasing cardiac contractility. At concentrations greater than 10 mg/kg some of the compounds of the present invention exhibit bronchodilator activity.

The 2-(4'-pyridinyl)-thiazole compounds of the present invention can be prepared in a variety of synthetic approaches with the preferred methods shown herein.

The alkyl2-(4'-pyridinyl)-thiazole-4-carboxylate can be conveniently prepared by condensing an appropriate thioisonicotinamide with an α-haloketoester, II.

The 4-carboxylate substituent may then be converted to the corresponding 4-carboxamide by treatment with ammonia or the appropriate amine.

The 4-carboxamide substituent can be converted to the 4-cyano substituent by reaction with either p-toluene sulfonyl chloride or phosphoryl chloride.

The starting materials employed are either commercially available or readily prepared by methods known in the art.

In the synthetic schemes depicted below, modification is shown on $R^5$. Modification on $R^6$ may be accomplished by using the same reactions shown for $R^5$.

SCHEME A

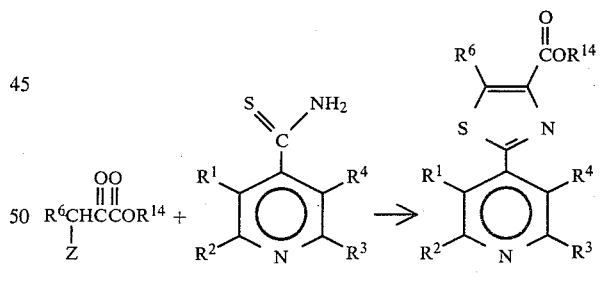

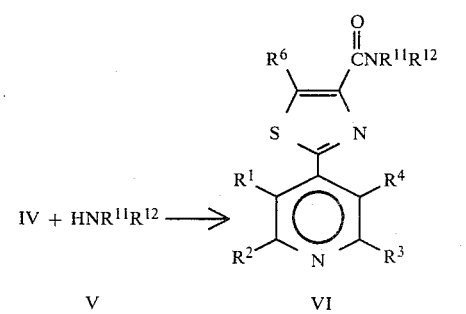

-continued
SCHEME A

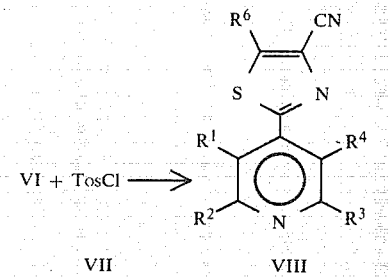

VI + TosCl → wherein $R^1$, $R^2$, $R^3$, $R^4$, $R^6$, $R^{11}$, $R^{12}$ are as defined above; TosCl represents p-toluene sulfonyl chloride; and Z is a halogen preferably bromine.

Reaction (1) is a conventional condensation reaction which is described in Chem Abstracts 70:37693Z and Liebigs Ann. Chem. 717, 148–153 (1968) which are incorporated herein by reference. The reaction can be conducted by adding an essentially equimolar amount of the appropriate thioisonicotinamide, III, to reagent II. The reaction is conducted in the liquid phase employing inert protic or aprotic solvents such as toluene, hydroxylic solvents (eg methanol, ethanol, water and the like), or a mixture of water and another hydroxylic solvent. Reaction pressure is not critical and for convenience the reaction is generally conducted at atmospheric pressure. The reaction is generally conducted at from 20° to 100° C., although preferably at the boiling point of the solvent employed, and is generally complete from within 1 to 72 hours. The resulting 2-(pyridinyl)thiazole, IV, or its hydrogen halide salt, is then isolated and purified by conventional procedures such as extraction, filtration, chromatography, distillation, or alternatively, can be used in reaction (2) without isolation and/or purification.

Reaction (2) can be accomplished by adding an excess of ammonia or the appropriate amine, V, to compound IV. The reaction is conducted in the liquid phase employing a inert hydroxylic solvent, water or a mixture of the hydroxylic solvent and water as the solvent. Alternatively, in lieu of a solvent, an excess of the amine, V, is employed. The reaction is generally conducted at pressures equal to or greater than atmospheric pressure and is generally complete within 72 hours. The resulting amide, VI, can then be isolated and purified by conventional procedures such as extraction, distillation, chromatagraphy, filtration, or alternatively, can be used in reaction (3) without isolation and/or purification.

The amide substituent, VI, is converted to the cyano substituent as shown in reaction (3). Reaction (3) is conducted by adding approximately 2 or more equivalents of p-toluene sulfonyl chloride to VI. The reaction is conducted in the liquid phase employing an inert organic solvent such as pyridine, dimethylformamide and the like. Alternateively, in lieu of employing p-toluene sulfonyl chloride and a solvent, an excess of phosphoryl chloride may be employed. Reaction pressure is not critical and for convenience the reaction is generally conducted at atmospheric pressure. The reaction is generally conducted at from 40° to 120° C., although preferably at from 80° to 110° C., and is generally complete from within 1 to 24 hours. The cyano-thiazole derivative, VIII, is then isolated and purified by conventional procedures such as extraction, distillation, filtration and the like.

Compounds of formula I wherein $R^5$ is hydroxy or trifluoromethyl can be prepared as shown in reaction (4) below:

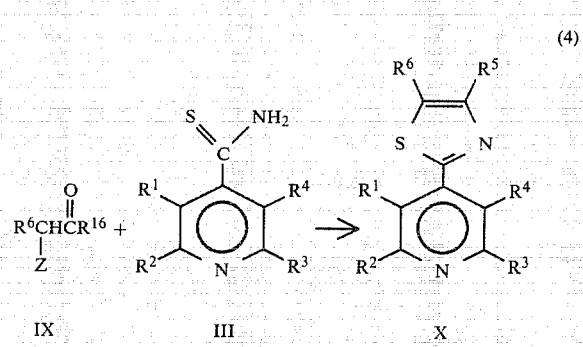

wherein $R^1$, $R^2$, $R^3$, $R^4$, $R^6$ and Z are as defined above and $R^{16}$ is hydroxy or trifluoromethyl. Reaction (4) may be conducted in the same manner as reaction (1) above to yield the 2-(pyridinyl)-thiazole derivatives, X.

The 2-(pyridinyl)thiazole, X, may be isolated and purified by conventional procedures such as extraction, filtration, chromatography, distillation and the like.

Compounds of Formula I wherein $R_6$ is hydroxy can be conveniently prepared by heterocyclization of an appropriate N-thioacyl derivative of amino acids with phosphorus tribromide or anhydrous trifluoroacetic acid. The reaction is described in *Heterocyclic Compounds, Thiazole and Its Derivatives*, Volume 34, part 2, ppg 426–428 (John Wiley & Sons, Ind., 1979).

The 4- or 5-hydroxy-thiazoles derivatives are tautomeric with the 4- and 5-oxo forms as shown below for the 5-hydroxy-thiazole:

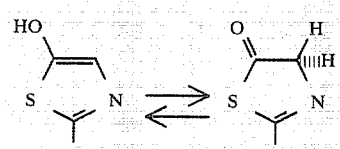

The tautomeric form of the thiazole is strongly solvent dependent (e.g. see *Heterocyclic Compounds, Thiazole and Its Derivatives*, Volume 34, part 2, pp 430–431 (John Wiley & Sons, Inc., 1979). Throughout this disclosure, the term 4-hydroxy-thiazole and 5-hydroxythiazole shall be taken to mean any of the above tautomers.

The 4- or 5-hydroxythiazole derivatives are readily converted to the corresponding 4- or 5-alkoxythiazole derivatives by methods well known in the art. For example, treatment of the hydroxy derivative with sodium hydride followed by addition of an alkyl halide yields the 4-alkoxy derivatives.

The amide, XIV, may be readily prepared from the ester, XI, by formation of the acyl hydrazide and treatment of the acyl hydrazide with nitrous acid and an acid anhydride as described in Liebigs Ann. Chem. 717, 148–153 (1968) and *Heterocyclic Compounds, Thiazole and its Derivatives*, Volume, 34 part 2, ppg 15–16 (John Wiley Sons, Inc. 1979) as shown in reaction (5) below, where $R^{17}$ is loweralkyl.

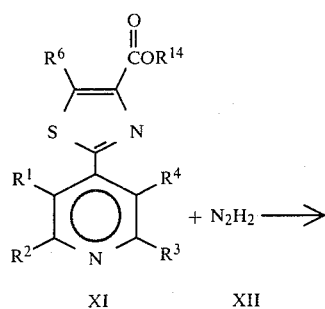

XI  XII

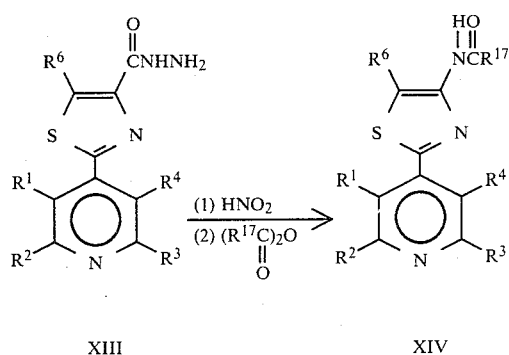

XIII  XIV

The amide, XIV, is readily converted to the amine, by base hydrolysis employing methods well known in the art.

Alternatively, the amide, XIV, may be alkylated by initially adding an essentially equimolar amount of a base, preferably sodium hydride, to the amide followed by addition of an essentially equimolar amount of an alkyl halide, R⁹Z, as shown in Reaction (6) below:

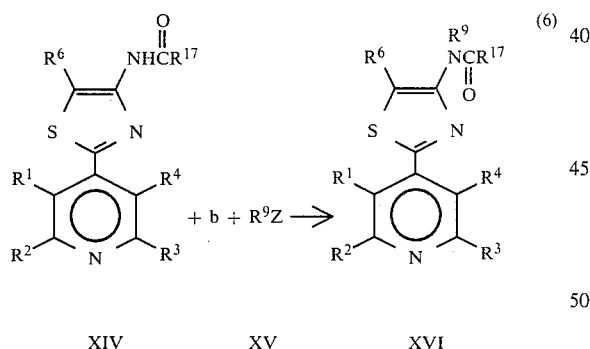

XIV  XV  XVI wherein $R^1$, $R^2$, $R^3$, $R^4$, $R^6$, $R^7$ and $R^{17}$ are as above defined and b is a base. The reaction is conducted in the liquid phase employing an inert aprotic solvent such as tetrahydrofuran and the like. The product, XVI, is then isolated by conventional procedures such as extraction, filtration, distillation, chromatography and the like.

The amides, XIV and XVI, are readily reduced to the corresponding amines by reduction methods well known in the art. For example, treatment of the amide, XVI, with lithium aluminum hydride yields the corresponding amine.

The pyridinyl N-oxide is prepared from the pyridinyl starting material by reaction with a oxidizing agent such as hydrogen peroxide, as shown below in reaction (7):

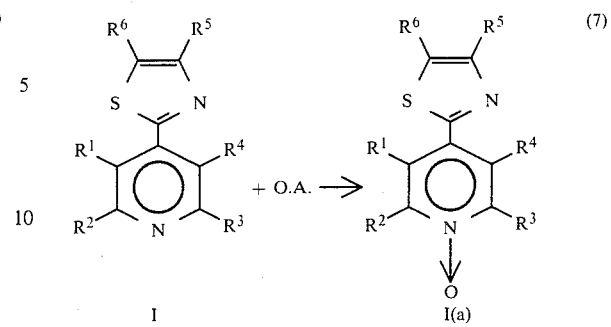

I  I(a)

where $R^1$, $R^2$, $R^3$, $R^4$, $R^5$ and $R^6$ are as defined above and O.A. represents an oxidizing agent capable of converting the nitrogen of pyridine to its N-oxide.

The reaction is accomplished by adding an excess of the oxidizing agent, preferably 30% hydrogen peroxide (in water), to the starting pyridinyl thiazole derivative, I. The reaction is conducted in the liquid phase employing an organic solvent which is miscible with water such as acetic acid. Reaction pressure is not critical and for convenience the reaction is generally conducted at atmospheric pressure. The reaction is generally conducted at from 50° to 100° C. and is generally complete from within 1 to 24 hours. The N-oxide, I(a), is then isolated and purified by conventional procedures such as distillation, filtration, chromatography, extraction and the like.

The cyanothiazole derivatives may be converted to the carboxamidine group as shown in reaction (9) below:

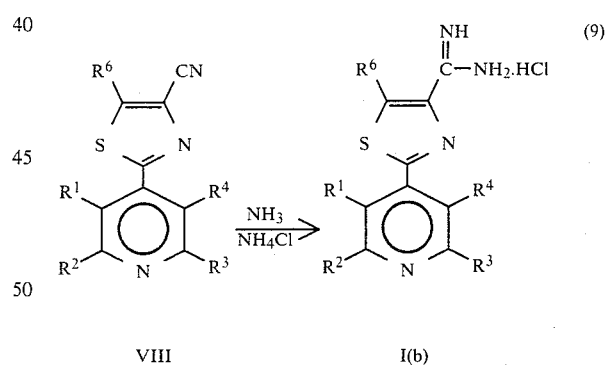

VIII  I(b)

The reaction is known in art and is described in Journal of Organic Chemistry Vol. 27 ppg 1255–1258 (1962) which is incorporated herewith by reference. The reaction is accomplished by treating the cyanothiazole derivative, VIII, with liquid ammonia and ammonium chloride in a steel bomb at elevated temperatures (80° C.). The product is then isolated and purified by conventional procedures such as extraction, chromatography, filtration and the like.

The cyanothiazole derivative may be converted to the thiocarboxamide group as shown in reaction (10) below:

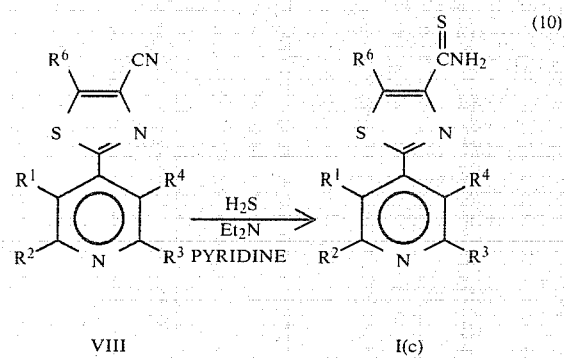

VIII                    I(c)

wherein $R^1$, $R^2$, $R^3$, $R^4$ and $R^6$ are as defined above. The reaction is known in the art and is described in J. Chem. Soc. ppg. 742-744 (1952). The reaction is accomplished by treating the cyano-thiazole, VIII, with hydrogen sulfide and triethylamine in pyridine at or above room temperature. The product, I(c), is then isolated and purified by conventional procedures such as extraction, distillation, chromatography, filtration and the like.

The following non-limiting examples describe in detail the preparation of the compounds and compositions of the present invention. As used herein the term "room temperature" refers to about 20° to 25° C. Unless otherwise stated, all temperature and temperature ranges are in degrees centigrade.

EXAMPLE 1

Preparation of 4-hydroxy-2-(4'-pyridinyl)-thiazole hydrobromide

Add 6.95 gm of bromoacetic acid to 70 ml of toluene along with 6.90 gm of thioisonicotinamide. Heat the system at reflux for 6 hours. Stop the reaction and cool the system to room temperature. Decant the toluene from the residue. Triturate the residue with absolute ethanol and then filter to yield 4-hydroxy-2-(4'-pyridinyl)-thiazole hydrobromide.

EXAMPLE 2

Preparation of N-ethyl 4-hydroxy-2-(4'-pyridinyl)-thiazole-5-carboxamide (a) Add 62.8 gm of diethyl bromomalonate to a suspension of 32.5 gm of thioisonicotinamide in 200 ml of absolute ethanol. Stir the system at room temperature for 72 hours. Stop the reaction and filter the solid. Recrystallize the solid from aqueous ethanol to yield ethyl 4-hydroxy-2-(4'-pyridinyl)-thiazole-5-carboxylate.

(b) Add 22.0 gm of ethyl 4-hydroxy-2-(4'-pyridinyl)-thiazole-5-carboxylate to 300 ml of 40% aqueous ethylamine in a steel bomb cooled to 0° to 5° C. Heat the system in an oil bath to 80° C. for 70 hours. Stop the reaction and cool the system to room temperature. Remove the solvent by stripping to yield a solid residue. Crystallize the residue from aqueous ethanol to give N-ethyl 4-hydroxy-2-(4'-pyridinyl)-thiazole-5-carboxamide.

EXAMPLE 3

Preparation of 2-(4'-pyridinyl)-thiazole-5-carboxamide (a) Add 18.0 gm of methyl chloroformylacetate to 18.2 gm of thioisonicotinamide in 250 ml of methanol. Heat the system to reflux for 22 hours. Stop the reaction and cool the system in an ice bath. Filter the solution to yield methyl 2-(4'-pyridinyl)-thiazole-5-carboxylate.

(b) Add 10.0 gm of methyl 2-(4'-pyridinyl)-thiazole-5-carboxylate to 200 ml of 20% ammonia in methanol in a steel bomb cooled to 0° to 5° C. Heat the system in an oil bath to 80° C. for 70 hours. Stop the reaction and cool the system to room temperature. Remove the solvent by stripping to yield a solid residue. Crystallize the residue from aqueous ethanol to give 2-(4'-pyridinyl)-thiazole-5-carboxamide.

EXAMPLE 4

Preparation of 4-methyl-2-(4'-pyridinyl)-thiazole-5-carboxamide (a) Add 10.3 gm of ethyl 2-chloroacetoacetate to 75 ml of methanol along with 17.3 gm of thioisonicotinamide. Heat the system to reflux for 4 hours. Stop the reaction and remove the solvent by stripping to yield a solid residue. Add 200 ml of toluene to the residue. Filter the solution and extract the filtrate first with 1N sodium hydroxide solution and then with 6N hydrochloric acid. Add concentrated ammonium hydroxide solution to the acid extract until the system is basic. Extract the product from this solution with chloroform. Dry the chloroform over anhydrous sodium sulfate and then filter the solution. Remove the chloroform by stripping to give a solid residue. Recrystallize the solid residue from 2-propanol to yield the ethyl 4-methyl-2-(4'-pyridinyl)-thiazole-5-carboxylate.

(b) Add 25.0 gm of ethyl 4-methyl-2-(4'-pyridinyl)-thiazole-5-carboxylate to 300 ml of 20% ammonia in methanol in a steel bomb cooled to 0° to 5° C. Heat the system in an oil bath to 80° C. for 70 hours. Stop the reaction and remove the solvent by stripping to yield a solid. Recrystallize the solid from aqueous ethanol to give the 4-methyl-2-(4'-pyridinyl)-thiazole-5-carboxamide.

EXAMPLE 5

Preparation of 2-(4'-pyridinyl)-thiazole-4-carboxamide (a) Add 70.0 gm of ethyl bromopyruvate to 41.5 gm of thioisonicotinamide in 600 ml of absolute ethanol. Heat the system at reflux for 2½ hours. Stop the reaction and cool the system to room temperature. Filter the solid from solution and recrystallize the solid from absolute ethanol to give the ethyl 2-(4'-pyridinyl)-thiazole-4-carboxylate hydrobromide ¼ hydrate.

(b) Add 25.0 gm of ethyl 2-(4'-pyridinyl)-thiazole-4-carboxylate hydrobromide ¼ hydrate to 300 ml of 20% ammonia in methanol in a steel bomb cooled to 0° to 5° C. Heat the system in an oil bath at 65° C. for 48 hours. Stop the reaction and cool the system to room temperature. Remove the solvent by stripping to yield a solid residue. Crystallize the residue from aqueous ethanol to give the 2-(4'-pyridinyl)-thiazole-4-carboxamide.

EXAMPLE 6

Preparation of N-methyl-2-(4'-pyridinyl)-thiazole-5-carboxamide

Add 5.5 gm of ethyl 2-(4'-pyridinyl)-thiazole-4-carboxylate hydrobromide ¼ hydrate to a steel bomb containing 40% aqueous methylamine. Heat the system in an oil bath at 100° C. for 16 hours. Stop the reaction and cool the system to room temperature. Extract the product with chloroform and wash the chloroform solution with water. Treat the chloroform solution with charcoal and then filter. Dry the chloroform solution with anhydrous sodium sulfate and filter. Remove the solvent by stripping to give the N-methyl-2-(4'-pyridinyl)-thiazole-4-carboxamide.

EXAMPLE 7

Preparation of 5-hydroxy-2-(4'-pyridinyl)-thiazole

Add 1 gm of N-thiocarbonyl-4-pyridinyl glycine to phosphorus tribromide. Stir the reaction at room temperature until the reaction is complete. Stop the reaction and isolate 5-hydroxy-2-(4'-pyridinyl)-thiazole.

EXAMPLE 8

Preparation of 4-ethoxy-2-(4'-pyridinyl)-thiazole

Add 4.8 gm of sodium hydride (50% by weight in oil) to 1.77 gm 4-hydroxy-2-(4'-pyridinyl)-thiazole in 100 ml of dimethylformamide. Heat the system to 110° C. for 4 hours. Cool the system to room temperature. Add 1.56 gm of ethyl iodide to the system. Stir the system at room temperature for 3 hours. Filter the solution and remove the solvent by stripping to give the 4-ethoxy-2-(4'-pyridinyl)thiazole.

Similarly, by following the same procedures as outlined in Examples 1 to 8 above and employing the appropriate reagents, the following compounds may be prepared:

N-ethyl 2-(4'-pyridinyl)thiazole-5-carboxamide;
N-ethyl 4-ethyl-2-(4'-pyridinyl)thiazole-5-carboxamide;
N-ethyl 4-n-propyl-2-(4'-pyridinyl)thiazole-5-carboxamide;
N-methyl 4-methyl-2-(4'-pyridinyl)thiazole-5-carboxamide;
N-n-propyl 5-methyl-2-(4'-pyridinyl)thiazole-4-carboxamide;
N-n-hexyl 5-ethyl-2-(4'-pyridinyl)thiazole-4-carboxamide;
N-methyl 5-n-propyl-2-(4'-pyridinyl)thiazole-4-carboxamide;
N,N-diethyl 5-propoxy-2-(4'-pyridinyl)thiazole-4-carboxamide;
N,N-dimethyl 5-methoxy-2-(4'-pyridinyl)thiazole-4-carboxamide;
N-ethyl N-methyl 5-cyano-2-(2',3'-dimethyl-4'-pyridinyl)-thiazole-4-carboxamide;
N-isopropyl 5-cyano-2-(3'-ethyl-4'-pyridinyl)thiazole-4-carboxamide;
5-methyl-4-trifluoromethyl-2-(2'-n-propyl-4'-pyridinyl)thiazole;
5-ethyl-4-trifluoromethyl-2-(2'-methyl-3'-chloro-4'-pyridinyl)thiazole;
4-hydroxy-2-(2'-methoxy-4'-pyridinyl)thiazole;
4-hydroxy-2-(2'-n-propoxy-4'-pyridinyl)thiazole;
4-hydroxy-2-(2'-hydroxy-3'-bromo-4'-pyridinyl)-thiazole;
5-hydroxy-2-(3'-hydroxy-4'-pyridinyl)thiazole;
N-Ethyl 5-(2"-hydroxyethyl)-2-(4'-pyridinyl)thiazole-4-carboxamide;
N-Methyl 5-methyl-2-(4'-pyridinyl)thiazole-4-carboxamide;
N,N-dimethyl 5-methyl-2-(3'-methyl-4'-pyridinyl)-thiazole-4-carboxamide;
N,N-diethyl 2-(3'-methyl-4'-pyridinyl)-thiazole-4-carboxamide;
N-n-hexyl-N-ethyl 2-(4'-pyridinyl)-thiazole-5-carboxamide;
N-isopropyl-N-ethyl 4-ethyl-2-(4'-pyridinyl)-thiazole-5-carboxamide;
N-ethyl 4-n-propyl-2-(4'-pyridinyl)-thiazole-5-carboxamide;
N-n-propyl 5-methyl-2-(4'-pyridinyl)-thiazole 4-carboxamide;
N-n-Hexyl 5-ethyl-2-(4'-pyridinyl)-thiazole-4-carboxamide;
N-ethyl 5-cyano-2-(4'-pyridinyl)-thiazole-4-carboxamide;
N-ethyl 4-hydroxy-2-(4'-pyridinyl)-thiazole-5-carboxamide;
5-hydroxy-4-methyl-2-(4'-pyridinyl)-thiazole.
2-(4'-pyridinyl)thiazole-5-carboxamide;
4-methyl-2-(4'-pyridinyl)thiazole-5-carboxamide;
N-ethyl-2-(4'-pyridinyl)thiazole-5-carboxamide;
N-methyl 5-methyl-2-(4'-pyridinyl)thiazole-4-carboxamide;
N,N-dimethyl 5-methyl-2-(4'-pyridinyl)thiazole-4-carboxamide;
N-ethyl 5-cyano-2-(4'-pyridinyl)thiazole-4-carboxamide;
N-(2"-hydroxyethyl) 5-methoxy-2-(4'-pyridinyl)-thiazole-4-carboxamide;
N-n-propyl 5-cyano-2-(3'-ethyl-4'-pyridinyl)-thiazole-4-carboxamide; and
N,N-di-n-propyl-5-methyl-2-(4'-pyridinyl)thiazole-4-carboxamide.

EXAMPLE 9

Preparation of 4-cyano-2-(4'-pyridinyl)thiazole

Add 10.8 gm of p-toluenesulfonyl chloride to 5.20 gm of 2-(4'-pyridinyl)-thiazole-4-carboxamide in 100 ml of pyridine cooled to 0° to 5° C. Heat the system to 90° C. in an oil bath for 18 hours. Remove the solvent by stripping and dissolve the residue in 200 ml of 1N hydrochloric acid. Extract the acid solution with chloroform. Cool the chloroform solution to 0° to 5° C. and then add 1N sodium hydroxide solution until the system is alkaline. Extract the product from this solution with chloroform. Wash the chloroform solution with water and then dry the chloroform solution with anhydrous magnesium sulfate. Filter the solution and remove the solvent by stripping to give the 4-cyano-2-(4'-pyridinyl)-thiazole.

EXAMPLE 10

Preparation of 4-methyl-5-cyano-2-(4'-pyridinyl)-thiazole

Add 10.0 gm of 4-methyl-2-(4'-pyridinyl)-thiazole-5-carboxamide to 100 ml of phosphoryl chloride. Heat the system at reflux for 6 hours. Remove the phosphoryl chloride by distillation at reduced pressure. Cool the residue to room temperature and then treat the residue with 300 ml 5% bicarbonate solution. Collect the resulting percipitate by filtration and dissolve the solid in 500 ml of chloroform. Treat the solution with charcoal and dry the solution over anhydrous magnesium sulfate. Filter and remove the solvent by stripping to give the 4-methyl-5-cyano-2-(4'-pyridinyl)-thiazole.

Similarly, by following the same procedures as outlined in Examples 9 and 10 above and employing the appropriate reagents, the following compounds can be prepared:

5-cyano-2-(4'-pyridinyl)-thiazole;
5-ethyl-4-cyano-2-(4'-pyridinyl)thiazole.

EXAMPLE 11

Preparation of N-acetyl-4-amino-2-(4'-pyridinyl)-thiazole hydrate (a) Add 5.9 gm of ethyl 2-(4'-pyridinyl)-thiazole-4-carboxylate to 100 ml of absolute ethanol along with 10 ml of 99–100% hydrazone hydrate. Stir the system at reflux for 16 hours. Remove the solvent by stripping to give a solid residue. Add 100 ml of chloroform to the residue and stir overnight. Filter the product from solution. Dissolve the product in isopropanol and treat the system with charcoal. Filter and recrystallize the product from the isopropanol to give 2-(4'-pyridinyl)-thiazole)-4-carbohydrazide.

(b) Add 2.20 gm of 2-(4'-pyridinyl)-thiazole-4-carbohydrazide to 30 ml of 2N hydrochloric acid at 5° C. Add 2.07 gm of sodium nitrite in portions at 5° C. Stir for ½ hour after addition of the sodium nitrite. Filter the solution and dry the solid over phosphorus pentoxide at reduced pressure. Add the solid azide to 6 ml of a 5:1 mixture of acetic anhydride/acetic acid. Heat the system to 95° C. and stir at 95° C. for ½ hour. Cool to 0° C. and then add water. Neutralize the solution with sodium carbonate. Filter the resulting suspension to give N-acetyl 4-amino-2-(4'-pyridinyl)-thiazole. Recrystallize this product from aqueous ethanol to give the title compound.

EXAMPLE 12

Preparation of 2-(4'-pyridinyl-N'-oxide)-thiazole-4-carboxamide

Add 1.42 ml of 30% hydrogen peroxide to 0.50 gm of 2-(4'-pyridinyl)-thiazole-4-carboxamide in 10 ml of glacial acetic acid at room temperature. Heat the system in an oil bath at 85° C. Add additional aliquots (1.0 ml) of 30% hydrogen peroxide until the reaction is complete as indicated by thin layer chromatography on silica gel eluted with ethyl acetate. Cool the system to room temperature and then add aqueous ethanol to give a suspension. Collect the product by filtration and air dry to give the 2-(4'-pyridinyl-N-oxide)-thiazole-4-carboxamide.

Similarly, by following the same procedure outlined in Example 12 above and employing the appropriate reagents, the following compounds can be prepared:
4-hydroxy-2-(2'-methoxy-4'-pyridinyl-N'-oxide)-thiazole;
5-hydroxy-2-(3'-hydroxy-4'-pyridinyl-N'-oxide)-thiazole;
5-hydroxy-4-methyl-2-(4'-pyridinyl-N'-oxide)-thiazole; and
5-ethyl-4-trifluoromethyl-2(2'-methyl-3'-chloro-4'-pyridinyl-N'-oxide)-thiazole.

EXAMPLE 13

Preparation of 4-amino-2-(4'-pyridinyl)-thiazole

Add 1.21 gm of N-acetyl 4-amino-2-(4'-pyridinyl)-thiazole to 60 ml of a 1:1 solution of 15% sodium hydroxide (in water)/methanol. Heat the system at reflux until complete. Remove the methanol by stripping. Extract the product with chloroform from the aqueous solution. Dry the chloroform solution over anhydrous magnesium sulfate. Filter the solution and remove the chloroform by stripping to give 4-amino-2-(4'-pyridinyl)-thiazole.

EXAMPLE 14

Preparation of N-ethyl-4-amino-2-(4'-pyridinyl)-thiazole

Add 2.37 gm of N-acetyl 4-amino-2-(4'-pyridinyl)-thiazole hydrate to 100 ml of diethyl ether. Cool the system to 0°–5° C. and then add 0.38 gm of lithium aluminum hydride to the system. Heat the system to 35° C. and stir at 35° C. for 4 hours. Stop the reaction isolate 4-(N-ethylamino)-2-(4'-pyridinyl)-thiazole.

Similarly, by following the same procedures as outlined in Example 14 above and employing the appropriate reagents the following compounds can be prepared:
N-n-propyl-4-amino-2-(4'-pyridinyl)-thiazole;
N,N-diethyl-4-amino-2-(4'-pyridinyl)-thiazole;
N,N-diethyl-5-amino-2-(4'-pyridinyl)-thiazole; and
N,N-di-n-propyl-5-amino-4-methyl-2-(4'-pyridinyl)-thiazole.

Similarly, by following the same procedures as outlined in Examples 11 and 13 above and employing the appropriate reagents the following compounds can be prepared:
4-amino-2-(3'-chloro-4'-pyridinyl)-thiazole;
5-amino-4-ethoxy-2-(4'-pyridinyl)-thiazole;
4-amino-5-ethoxy-2-(4'-pyridinyl)-thiazole; and
5-amino-4-methyl-2-(4'-pyridinyl)-thiazole.

EXAMPLE 15

Preparation of 2-(4'-pyridinyl)-thiazole-4-carboxamidine hydrochloride

Add 1.87 gm of 4-cyano-2-(4'-pyridinyl)-thiazole to 0.53 gm ammonium chloride in liquid ammonia in a steel bomb. Heat the system to 80° C. for 24 hours Cool the system to room temperature and remove the ammonia. Isolate the 2-(4'-pyridinyl)-thiazole-4-carboxamidine hydrochloride.

Similarly, by following the same procedures as outlined in Example 15 above and employing the appropriate reagents, the following compounds can be prepared:
2-(4'-pyridinyl)-thiazole-5-carboxamidine hydrochloride;
4-methyl-2-(4'-pyridinyl)-thiazole-5-carboxamidine hydrochloride;
4-ethyl-2-(4'-pyridinyl)-thiazole-5-carboxamidine hydrochloride; and
5-ethyl-2-(4'-pyridinyl)-thiazole-4-carboxamidine hydrochloride

EXAMPLE 16

Preparation of 2-(4'-pyridinyl)-thiazole-4-thiocarboxamide

Dissolve 2.0 gm of 4-cyano-2-(4-pyridinyl)-thiazole in 25.0 gm of pyridine. Add 1.5 ml of triethylamine to the system. Cool the system to 0°–5° C. and treat the system with hydrogen sulfide gas until the reaction is complete as indicated by thin layer chromatography. Pour the reaction mixture into icewater and filter to give 2-(4'-pyridinyl)-thiazole 4thiocarboxamide.

Similarly, by following the same procedures as outlined in Example 16 and employing the appropriate reagents, the following compounds can be prepared:
5-methyl-2-(4'-pyridinyl)-thiazole-4-thiocarboxamide;
4-methoxy-2-(3'-chloro-4'-pyridinyl)-thiazole-4-thiocarboxamide; and
2-(4'-pyridinyl)-thiazole-5-thiocarboxamide.

The following formulations exemplify some of the dosage forms in which the compounds of this invention may be employed. In each, the active ingredient is designated by the term "Drug" which is meant to indicate one of the following compounds:
4-cyano-2-(4'-pyridinyl)-thiazole;
2-(4'-pyridinyl)-thiazole-4-carboxamide; and
2-(4'-pyridinyl)-thiazole-5-carboxamide.

It is contemplated, however, that each of these exemplar compounds may be replaced by equally effective quantities of other compounds within the scope of Formula I. All temperatures are in degrees Celsius.

EXAMPLE 17

Capsules

| No. | Ingredient | mg/capsule | mg/capsule |
|---|---|---|---|
| 1. | Drug | 250 | 500 |
| 2. | Lactose USP | 100 | 50 |
| 3. | Corn Starch, Food Grade | 50 | 43.5 |
| 4. | Microcrystalline Cellulose | 95 | 50 |
| 5. | Magnesium Stearate NF | 5 | 6.5 |
|   | Total | 500 | 650 |

Method of Manufacture

Mix Item Nos. 1, 2, 3 and 4 in a suitable mixer for 10-15 minutes. Add Item No. 5 and mix for 1-3 minutes. Fill the mixture into suitable two-piece hard gelatin capsules using suitable encapsulaing machine.

EXAMPLE 18

Tablets

| No. | Ingredient | mg/tablet | mg/tablet |
|---|---|---|---|
| 1 | Drug | 250 | 500 |
| 2. | Lactose USP | 57 | 114 |
| 3. | Corn Starch, Food Grade, as a 10% paste in Purified Water | 20 | 40 |
| 4. | Corn Starch, Food Grade | 18 | 39 |
| 5. | Magnesium Stearate NF | 5 | 7 |
|   | Total | 350 | 700 |

Method of Manufacture

Mix Item Nos. 1 and 2 in a suitable mixer for 10-15 minutes. Granulate the mixture with Item No. 3. Pass the wet granulation through a coarse screen (e.g., ¼") if needed, and dry the wet granules. Mill the dried granules.

Combine Item No. 4 and the dried granules and mix for 10-15 minutes. Add Item No. 5 and mix for 1-3 minutes. Compress the mixture to appropriate size and weight on a suitable tablet machine.

EXAMPLE 19

Parenteral Dosage Forms (a) Injection (Per vial)

|   | mg/vial |
|---|---|
| Drug Sterile Powder | 500 |

Add sterile water for injection or bacteriostatic water for injection for reconstitution.

(b) Injectable Solution of drug

| Ingredient | mg/ml |
|---|---|
| Drug | 20 |
| Methylparaben | 0.2 |
| Propylparaben | 1.6 |
| Sodium Bisulfite | 3.2 |
| Disodium Edetate | 0.1 |
| Water for Injection q.s. ad | 1.0 ml |

Method of Manufacture

1. Dissolve parabens in a portion (85% of the final volume) of the water for injection at 65°-70° C.
2. Cool to 25°-35° C. Charge and dissolve the sodium bisulfite and disodium edetate.
3. Charge and dissolve Drug.
4. Bring the solution to final volume by adding water for injection.
5. Filter the solution through 0.22 membrane and fill into appropriate containers.
6. Terminally sterilize the units by autoclaving.

We claim:

1. A compound of the formula:

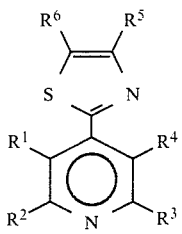

wherein
$R^1$, $R^2$, $R^3$ and $R^4$ are independently selected from
(i) hydrogen,
(ii) halogen,
(iii) lower alkyl,
(iv) lower alkoxy,
(v) hydroxy, and
(vi) amino,
$R^5$ and $R^6$ are independently selected from
(i) hydrogen with the proviso that $R^5$ and $R^6$ are not both hydrogen,
(ii) lower alkyl with the proviso that when $R^1$, $R^2$, $R^3$, $R^4$ and $R^6$ are hydrogen and $R^5$ is not lower alkyl,
(iii) lower alkoxy,
(iv) hydroxy, with the proviso that when $R^1$, $R^2$, $R^3$ and $R^4$ are hydrogen and $R^5$ is hydroxy, $R^6$ is not lower alkyl,
(v) —$NR^7R^8$ wherein $R^7$ and $R^8$ are the same or different and are independently selected from lower alkyl or hydrogen,
(vi) trifluoromethyl,
(vii) hydroxy lower alkyl,
(viii) cyano,
(ix)

wherein $R^{11}$ and $R^{12}$ are the same or different and are independently selected from hydrogen, lower alkyl and hydroxy lower alkyl, and Y is sulfur or oxygen, (x)

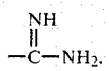

(C) the pyridinyl N-oxides thereof; and
(D) pharmaceutically acceptable salts thereof.

2. A compound of the formula defined in claim 1 wherein $R^5$ is hydrogen, amino, cyano, hydroxy, or

wherein $R^{11}$ and $R^{12}$ are the same or different and are independently selected from hydrogen, lower alkyl and hydroxy lower alkyl.

3. A compound of the formula defined in claim 2 wherein $R^5$ is

wherein $R^{11}$ and $R^{12}$ are the same or different and are independently selected from hydrogen or lower alkyl.

4. A compound of the formula defined in claim 3 wherein $R^5$ is

5. A compound of the formula defined in claim 1 wherein $R^6$ is hydrogen, lower alkyl, cyano, hydroxy, or

wherein $R^{11}$ and $R^{12}$ are the same or different and are independently selected from hydrogen, lower alkyl and hydroxy lower alkyl.

6. A compound of the formula defined in claim 5 wherein $R^6$ is

wherein $R^{11}$ and $R^{12}$ are the same or different and are independently selected from hydrogen or lower alkyl.

7. A compound of the formula defined in claim 1 wherein $R^1$, $R^2$, $R^3$ and $R^4$ are hydrogen.

8. A compound of the formula defined in claim 7 wherein $R^6$ is hydrogen.

9. A compound of the formula defined in claim 8 wherein $R^5$ is cyano, i.e. 4-cyano-2-(4'-pyridinyl)-thiazole.

10. A compound of the formula defined in claim 9 wherein $R^5$ is

i.e. 2-(4'-pyridinyl)-thiazole-4-carboxamide.

11. A pharmaceutical composition comprising a pharmaceutically acceptable carrier and an amount effective in increasing cardiotonic contractility of a compound of the formula:

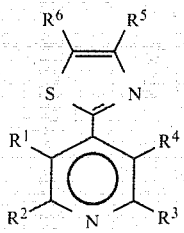

wherein
(A) $R^1$, $R^2$, $R^3$ and $R^4$ are independently selected from
  (i) hydrogen,
  (ii) halogen,
  (iii) lower alkyl,
  (iv) lower alkoxy,
  (v) hydroxy, and
  (vi) amino,
(B) $R^5$ and $R^6$ are independently selected from
  (i) hydrogen with the proviso that $R^5$ and $R^6$ are not both hydrogen,
  (ii) lower alkyl with the proviso that when $R^1$, $R^2$, $R^3$, $R^4$ and $R^6$ are hydrogen, $R^5$ is not lower alkyl,
  (iii) lower alkoxy,
  (iv) hydroxy, with the proviso that when $R^1$, $R^2$, $R^3$ and $R^4$ are hydrogen and $R^5$ is hydroxy, $R^6$ is not lower alkyl,
  (v) $-NR^7R^8$ wherein $R^7$ and $R^8$ are the same or different and are independently selected from lower alkyl or hydrogen,
  (vi) trifluoromethyl,
  (vii) hydroxy lower alkyl,
  (viii) cyano,
  (ix)

wherein $R^{11}$ and $R^{12}$ are the same or different and are independently selected from hyrogen, lower alkyl and hydroxy lower alkyl, and Y is sulfur or oxygen,
(x)

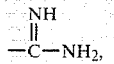

(C) the pyridinyl N-oxides thereof; and
(D) pharmaceutically acceptable salts thereof.

12. A pharmaceutical composition comprising a pharmaceutically acceptable carrier and an amount effective in increasing cardiac contractility of the compound of formula defined in claim 9.

13. A pharmaceutical composition comprising a pharmaceutically acceptable carrier and an amount effective in increasing cardiac of the compound of the formula defined in claim 10.

14. A method for increasing cardiac contractility in a patient requiring such treatment which comprises administering either orally or parenterally an amount effective in increasing cardiac contractility of a compound of the formula defined in claim 1.

15. A method for increasing cardiac contractility in a patient requiring such treatment which comprises administering either orally or parenterally an amount effective in increasing cardiac contractility of the compound of the formula defined in claim 9.

16. A method for increasing cardiac contractility inh a patient requiring such treatment which comprises administering either orally or parenterally an amount effective in increasing cardiac contractility of the compound of the formula defined in claim 10.

17. A compound of the formula defined in claim 1 wherein $R^1$, $R^2$, $R^3$ and $R^4$ are the same or different and are independently selected from hydrogen and lower alkyl.

18. A compound of the formula defined in claim 1 wherein Y is oxygen.

19. A compound of the formula defined in claim 8 wherein Y is oxygen.

* * * * *